(12) United States Patent
Foster et al.

(10) Patent No.: US 9,404,838 B2
(45) Date of Patent: *Aug. 2, 2016

(54) PARTICLE MANIPULATION SYSTEM WITH OUT-OF-PLANE CHANNEL AND FOCUSING ELEMENT

(71) Applicant: Owl biomedical, Inc., Goleta, CA (US)

(72) Inventors: John S Foster, Santa Barbara, CA (US); Nicholas C. Martinez, Santa Barbara, CA (US); Stefan Miltenyi, Bergische Gladbach (DE); Kamala R. Qalandar, Ojai, CA (US); Kevin E. Shields, Santa Barbara, CA (US); Kimberly L. Turner, Santa Barbara, CA (US); Mehran R. Hoonejani, Goleta, CA (US)

(73) Assignee: Owl biomedical, Inc., Goleta, CA (US)

( * ) Notice: Subject to any disclaimer, the term of this patent is extended or adjusted under 35 U.S.C. 154(b) by 262 days.

This patent is subject to a terminal disclaimer.

(21) Appl. No.: 13/998,096

(22) Filed: Oct. 1, 2013

(65) Prior Publication Data

US 2015/0093810 A1    Apr. 2, 2015

(51) Int. Cl.
*G01N 33/00*  (2006.01)
*G01N 1/40*  (2006.01)
(Continued)

(52) U.S. Cl.
CPC ........ *G01N 1/4077* (2013.01); *B01L 3/502738* (2013.01); *B01L 3/502761* (2013.01); *F16K 99/0011* (2013.01); *F16K 99/0013* (2013.01); *F16K 99/0028* (2013.01); *F16K 99/0046* (2013.01); *G01N 15/1459* (2013.01); *G01N 15/1484* (2013.01); *B01L 2200/0652* (2013.01);
(Continued)

(58) Field of Classification Search
CPC .................. G01N 1/4077; G01L 3/502738
See application file for complete search history.

(56) References Cited

U.S. PATENT DOCUMENTS

| 6,431,476 B1 | 8/2002 | Taylor |
| 6,686,299 B2 | 2/2004 | Montemagno |

(Continued)

FOREIGN PATENT DOCUMENTS

| WO | WO 2006/076567 | 7/2006 |
| WO | WO 2008/130977 | 10/2008 |

OTHER PUBLICATIONS

"Single-layer planar on-chip flow cytometer using microfluidic drifting based three-dimensional (3D) hydrodynamic focusing," Xiaole Mao, et al. Journal of Royal Society of Chemistry, Lab Chip, 2009, 9, 1583-1589.

(Continued)

*Primary Examiner* — Sam P Siefke
(74) *Attorney, Agent, or Firm* — Jaquelin K. Spong

(57) ABSTRACT

A particle manipulation system uses a MEMS-based, microfabricated particle manipulation device which has an inlet channel, output channels, and a movable member formed on a substrate. The movable member moves parallel to the fabrication plane, as does fluid flowing in the inlet channel. The movable member separates a target particle from the rest of the particles, diverting it into an output channel. However, at least one output channel is not parallel to the fabrication plane. The device may be used to separate a target particle from non-target material in a sample stream. The target particle may be, for example, a stem cell, zygote, a cancer cell, a T-cell, a component of blood, bacteria or DNA sample, for example. The particle manipulation system may also include a microfluidic structure which focuses the target particles in a particular portion of the inlet channel.

17 Claims, 13 Drawing Sheets

(51) Int. Cl.
  *B01L 3/00* (2006.01)
  *F16K 99/00* (2006.01)
  *G01N 15/10* (2006.01)
  *G01N 15/14* (2006.01)

(52) U.S. Cl.
  CPC .. *B01L 2300/0654* (2013.01); *B01L 2400/0487* (2013.01); *B01L 2400/0622* (2013.01); *B01L 2400/0633* (2013.01); *F16K 2099/0084* (2013.01); *F16K 2099/0086* (2013.01); *G01N 2015/1006* (2013.01); *G01N 2015/149* (2013.01)

(56) References Cited

U.S. PATENT DOCUMENTS

| | | | |
|---|---|---|---|
| 6,838,056 | B2 | 1/2005 | Foster |
| 6,941,005 | B2 | 9/2005 | Lary et al. |
| 7,220,594 | B2 | 5/2007 | Foster et al. |
| 7,229,838 | B2 | 6/2007 | Foster et al. |
| 7,264,972 | B2 | 9/2007 | Foster |
| 7,390,648 | B1 | 6/2008 | Palacios-Boyce |
| 7,569,789 | B2 | 8/2009 | Hayenga et al. |
| 7,704,743 | B2 | 4/2010 | Fedorov et al. |
| 7,745,221 | B2 | 6/2010 | Butler et al. |
| 8,120,770 | B2 | 2/2012 | Huang et al. |
| 2007/0178529 | A1* | 8/2007 | Breidford ............... B01F 11/04 435/7.1 |
| 2009/0014360 | A1 | 1/2009 | Toner et al. |
| 2012/0196314 | A1 | 8/2012 | Nawaz et al. |

OTHER PUBLICATIONS

"Inertial microfluidics," Di Carlo, Journal of Royal Society of Chemistry, Lab Chip, 2009, 9, 3038-3046.

"Microfluidic drilling"—implementing three-dimensional hydrodynamic focusing with a single-layer planar microfluidic device, Xiaole Mao, et al. Journal of Royal Society of Chemistry, Lab Chip, 2007, 7, 1260-1262.

U.S. Appl. No. 13/374,899, filed Jan. 23, 2012, Foster, et al.

U.S. Appl. No. 13/374,898, filed Jan. 23, 2012, Foster, et al.

Xiaole Mao, et al. "Single-layer planar on-chip flow cytometer using microfluidic drifting based three-dimensional (3D) hydrodynamic focusing," Lab on a Chip, vol. 9, No. 11 Jan. 1, 2009, p. 1583.

* cited by examiner

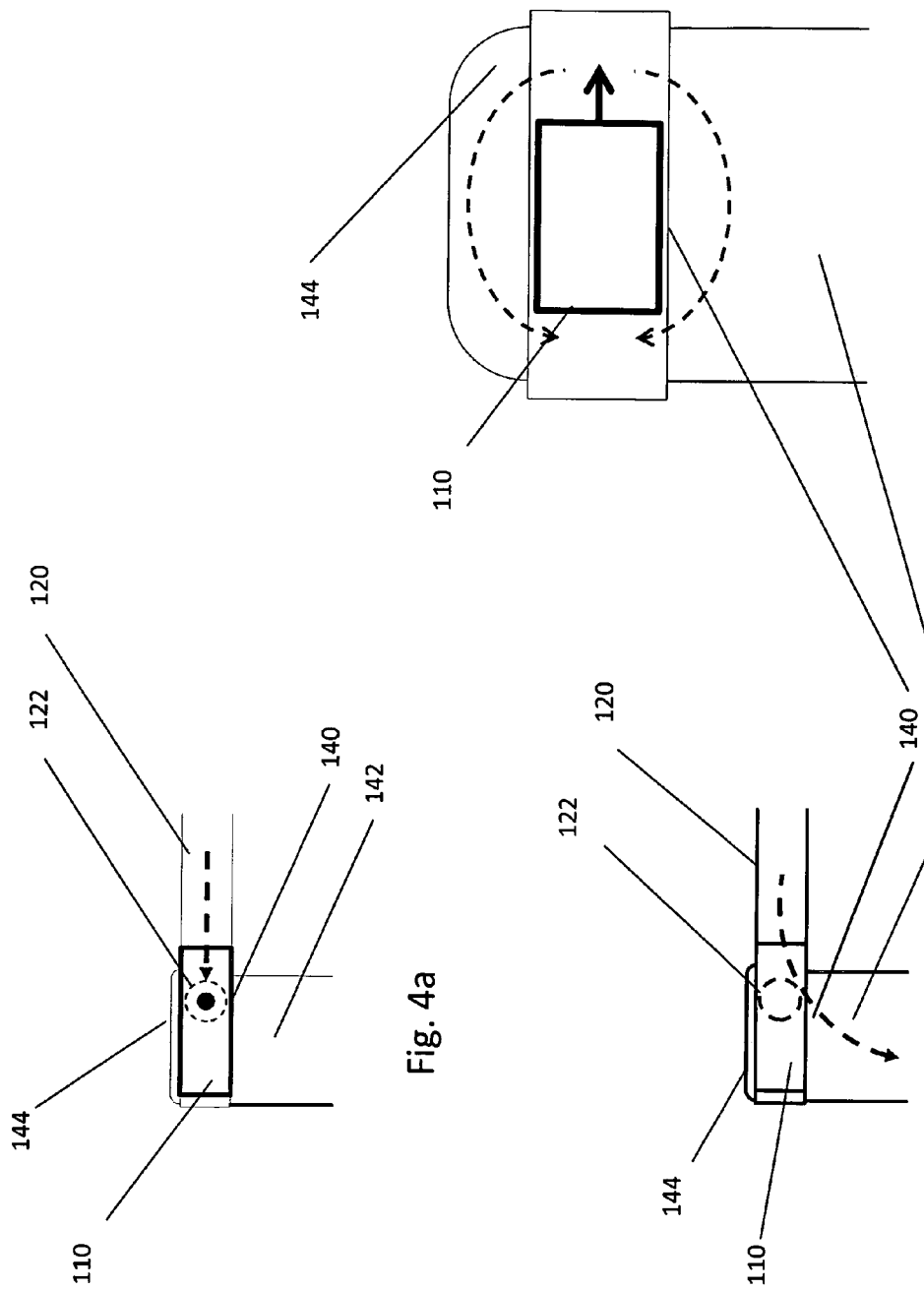

US 9,404,838 B2

PARTICLE MANIPULATION SYSTEM WITH OUT-OF-PLANE CHANNEL AND FOCUSING ELEMENT

CROSS REFERENCE TO RELATED APPLICATIONS

Not applicable.

STATEMENT REGARDING FEDERALLY SPONSORED RESEARCH Not applicable.

STATEMENT REGARDING MICROFICHE APPENDIX

Not applicable.

BACKGROUND

This invention relates to a system and method for manipulating small particles in a microfabricated fluid channel.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example. MEMS devices may be fabricated on a semiconductor substrate which may manipulate particles passing by the MEMS device in a fluid stream.

In another example, a MEMS devices may be a movable valve, used as a sorting mechanism for sorting various particles from a fluid stream, such as cells from blood. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

MEMS-based cell sorter systems may have substantial advantages over existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between sample, inability to re-sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

A number of patents have been granted which are directed to such MEMS-based particle sorting devices. For example, U.S. Pat. No. 6,838,056 (the '056 patent) is directed to a MEMS-based cell sorting device, U.S. Pat. No. 7,264,972 b1 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Additionally, U.S. patent application Ser. No. 13/374,899 (the '899 application) and Ser. No. 13/374,898 (the '898 application) provide further details of other MEMS designs. Each of these patents ('056, '972, '594 and '838) and patent applications ('898 and '899) is hereby incorporated by reference.

SUMMARY

One feature of the MEMS-based microfabricated particle sorting system is that the fluid may be confined to small, microfabricated channels formed in a semiconductor substrate throughout the sorting process. The MEMS device may be a valve which separates one or more target particles from other components of a sample stream. The MEMS device may redirect the particle flow from one channel into another channel, when a signal indicates that a target particle is present. This signal may be photons from a fluorescent tag which is affixed to the target particles and excited by laser illumination in an interrogation region upstream of the MEMS device. Thus, the MEMS device may be a particle or cell sorter operating on a fluid sample confined to a microfabricated fluidic channel, but using detection means similar to a FACS flow cytometer. In particular, the '898 application discloses a microfabricated fluidic valve wherein the inlet channel, sort channel and waste channel all flow in a plane parallel to the fabrication plane of the microfabricated fluidic valve.

A substantial improvement may be made over the prior art devices by having at least one of the microfabricated fluidic channels route the flow out of the plane of fabrication of the microfabricated valve. A valve with such an architecture has the advantage that the pressure resisting the valve movement is minimized when the valve opens or closes, because the movable member is not required to move a column of fluid out of the way. Instead, the fluid containing the non-target particles may move over and under the movable member to reach the waste channel. Furthermore, the force-generating apparatus may be disposed closer to the movable valve, resulting in higher forces and faster actuation speeds. As a result, the time required to open or close the valve may be much shorter than the prior art valve, improving sorting speed and accuracy. The systems and methods disclosed here may describe such a microfabricated particle sorting device with at least one out-of-plane channel.

In the systems and methods disclosed here, a micromechanical particle manipulation device may be formed on a surface of a fabrication substrate, wherein the micromechanical particle manipulation device may include a microfabricated, movable member having a first diverting surface, wherein the movable member moves from a first position to a second position in response to a force applied to the movable member, wherein the motion is substantially in a plane parallel to the surface, a sample inlet channel formed in the substrate and through which a fluid flows, the fluid including at least one target particle and non-target material, wherein the flow in the sample inlet channel is substantially parallel to the surface, and a plurality of output channels into which the microfabricated member diverts the fluid, and wherein the flow in at least one of the output channels is not parallel to the plane, wherein at least one output channel is located directly below at least a portion of the microfabricated diverter over at least a portion of its motion. In one embodiment, The micromechanical particle manipulation device of claim 1, wherein the first diverting surface has a smoothly curved shape which is substantially tangent to the direction of flow in the inlet channel at one point on the shape and substantially tangent to the direction of flow of a first output channel at a second point on the shape, wherein the first diverting surface diverts flow from the inlet channel into the first output channel when the movable member is in the first position, and allows the flow into a second output channel in the second position.

Finally, the systems and methods disclosed herein, because they include microfabricated channels as well as the novel valve design, may allow additional useful features to be implemented. For example, the techniques may form a particle manipulation system with cytometric capability, as described in co-pending U.S. patent application Ser. No. 13/507,830 (Owl-Cytometer) filed Aug. 1, 2012 and assigned to the same assignee as the present application. This patent application is incorporated by reference in its entirety. The MEMS device describe here may be used to manipulate the particles in the fluid stream enclosed in the microfabricated channel, while a plurality of interrogation regions also exist which may provide feedback on the manipulation. For example, in the case of cell sorting, one laser interrogation region may exist upstream of the MEMS device, and at least one additional laser interrogation region may exist downstream of the MEMS device, to confirm the results of the particle manipulation, that the correct cell has been sorted.

The systems and methods disclosed here also enable the construction of a single-input/double output sorting device, wherein the flow from a single input channel can be diverted into either of two sort output channels, or allowed to flow through to the waste channel.

In another embodiment, the novel valve architecture may make use of hydrodynamic particle focusing techniques, as taught by, for example, " Single-layer planar on-chip flow cytometer using microfluidic drifting based three-dimensional (3D) hydrodynamic focusing," by Xaiole Mao, et al. (hereinafter "Mao," Journal of Royal Society of Chemistry, Lab Chip, 2009, 9, 1583-1589). The microfabricated architecture of the systems and methods disclosed herein make them especially suitable for the techniques disclosed in Mao, as described further below.

These and other features and advantages are described in, or are apparent from, the following detailed description.

BRIEF DESCRIPTION OF THE DRAWINGS

Various exemplary details are described with reference to the following figures, wherein:

FIG. 4a is a simplified cross sectional view of a microfabricated particle sorting system in the actuated (sort) position, showing the flow of the sample stream into the sort channel which is in the same plane as the inlet channel; FIG. 4b is a simplified cross sectional view of a microfabricated particle sorting system in the quiescent (no sort) position, showing the flow of the sample stream into the waste channel which is not in the same plane as the inlet channel; FIG. 4c is a simplified cross sectional view of a microfabricated particle sorting system in the quiescent (no sort) position, showing the flow of the sample stream into the waste channel which is not in the same plane as the inlet channel, wherein the sample stream flows around the top and the bottom of the diverter;

DETAILED DESCRIPTION

The system described herein is a particle sorting system which may make use of the microchannel architecture of a MEMS particle manipulation system. More generally, the systems and methods describe a particle manipulation system with an inlet channel and a plurality of output channels, wherein at least one of the plurality of output channels is disposed in a different plane than the inlet channel. This architecture has some significant advantages relative to the prior art.

In the figures discussed below, similar reference numbers are intended to refer to similar structures, and the structures are illustrated at various levels of detail to give a clear view of the important features of this novel device. It should be understood that these drawings do not necessarily depict the structures to scale, and that directional designations such as "top," "bottom," "upper," "lower," "left" and "right" are arbitrary, as the device may be constructed and operated in any particular orientation. In particular, it should be understood that the designations "sort" and "waste" are interchangeable, as they only refer to different populations of particles, and which population is called the "target" or "sort" population is arbitrary.

Figure 1:
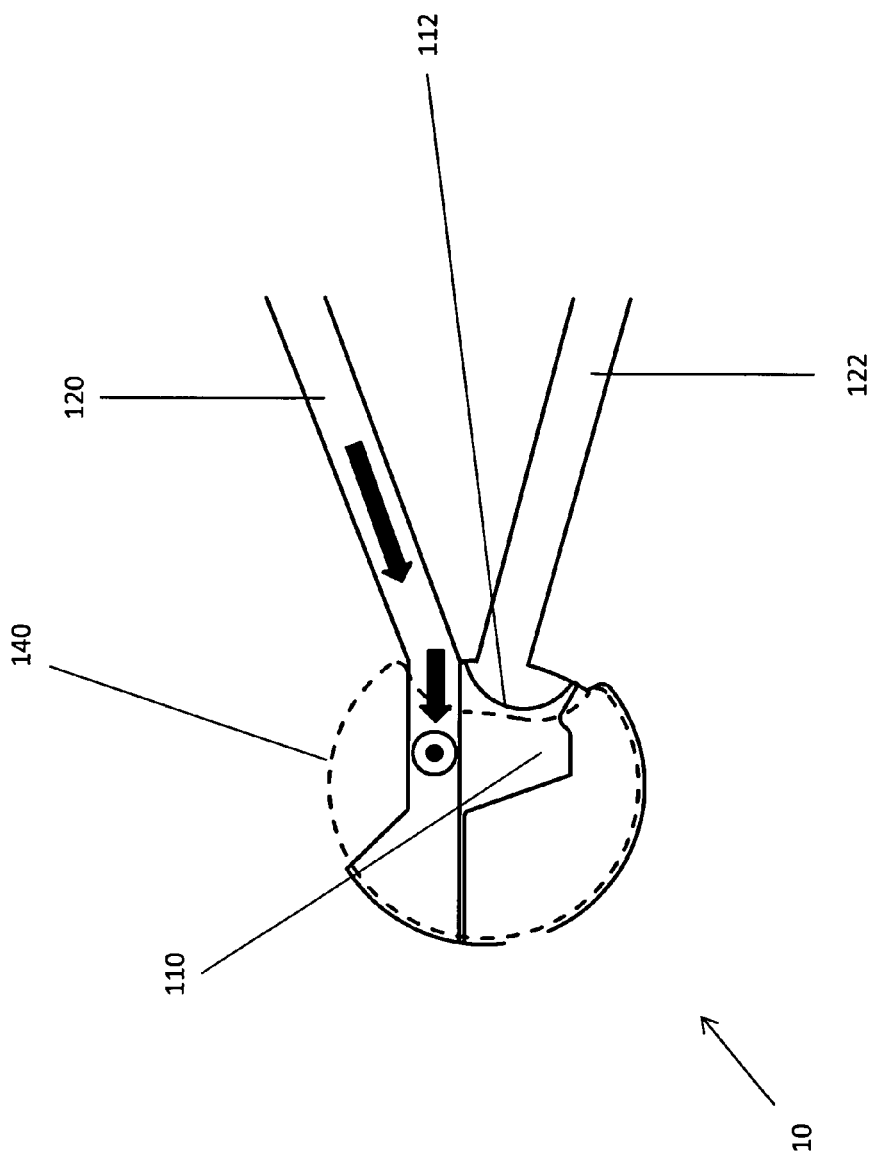
FIG. 1 is a simplified plan view of a microfabricated particle sorting system in the quiescent (no sort) position.

FIG. 1 is an plan view illustration of the novel microfabricated fluidic device 10 in the quiescent (un-actuated) position. The device 10 may include a microfabricated fluidic valve or movable member 110 and a number of microfabricated fluidic channels 120, 122 and 140. The fluidic valve 110 and microfabricated fluidic channels 120, 122 and 140 may be formed in a suitable substrate, such as a silicon substrate, using MEMS lithographic fabrication techniques as described in greater detail below. The fabrication substrate may have a fabrication plane in which the device is formed and in which the movable member 110 moves.

A sample stream may be introduced to the microfabricated fluidic valve 110 by a sample inlet channel 120. The sample stream may contain a mixture of particles, including at least one desired, target particle and a number of other undesired, nontarget particles. The particles may be suspended in a fluid. For example, the target particle may be a biological material such as a stem cell, a cancer cell, a zygote, a protein, a T-cell, a bacteria, a component of blood, a DNA fragment, for example, suspended in a buffer fluid such as saline. The inlet channel 120 may be formed in the same fabrication plane as the valve 110, such that the flow of the fluid is substantially in that plane. The motion of the valve 110 is also within this fabrication plane. The decision to sort/save or dispose/waste a given particle may be based on any number of distinguishing signals. In one exemplary embodiment, the decision is based on a fluorescence signal emitted by the particle, based on a fluorescent tag affixed to the particle and excited by an illuminating laser. Details as to this detection mechanism are well known in the literature, and further discussed below with respect to FIG. 12. However, other sorts of distinguishing signals may be anticipated, including scattered light or side scattered light which may be based on the morphology of a particle, or any number of mechanical, chemical, electric or magnetic effects that can identify a particle as being either a target particle, and thus sorted or saved, or an nontarget particle and thus rejected or otherwise disposed of.

With the valve 110 in the position shown, the input stream passes unimpeded to an output orifice and channel 140 which is out of the plane of the inlet channel 120, and thus out of the fabrication plane of the device 10. That is, the flow is from the inlet channel 120 to the output orifice 140, from which it flows substantially vertically, and thus orthogonally to the inlet channel 120. This output orifice 140 leads to an out-of-plane channel that may be perpendicular to the plane of the paper showing FIG. 1, and depicted in the cross sectional views of FIGS. 4a-4c. More generally, the output channel 140 is not parallel to the plane of the inlet channel 120 or sort channel 122, or the fabrication plane of the movable member 110.

The output orifice 140 may be a hole formed in the fabrication substrate, or in a covering substrate that is bonded to the fabrication substrate. A relieved area above and below the sorting valve or movable member 110 allows fluid to flow above and below the movable member 110 to output orifice 140, and shown in more detail in FIGS. 4a-4c. Further, the valve 110 may have a curved diverting surface 112 which can redirect the flow of the input stream into a sort output stream, as described next with respect to FIG. 2. The contour of the orifice 140 may be such that it overlaps some, but not all, of the inlet channel 120 and sort channel 122. By having the contour 140 overlap the inlet channel, and with relieved areas described above, a route exists for the input stream to flow directly into the waste orifice 140 when the movable member or valve 110 is in the un-actuated waste position.

Figure 2:
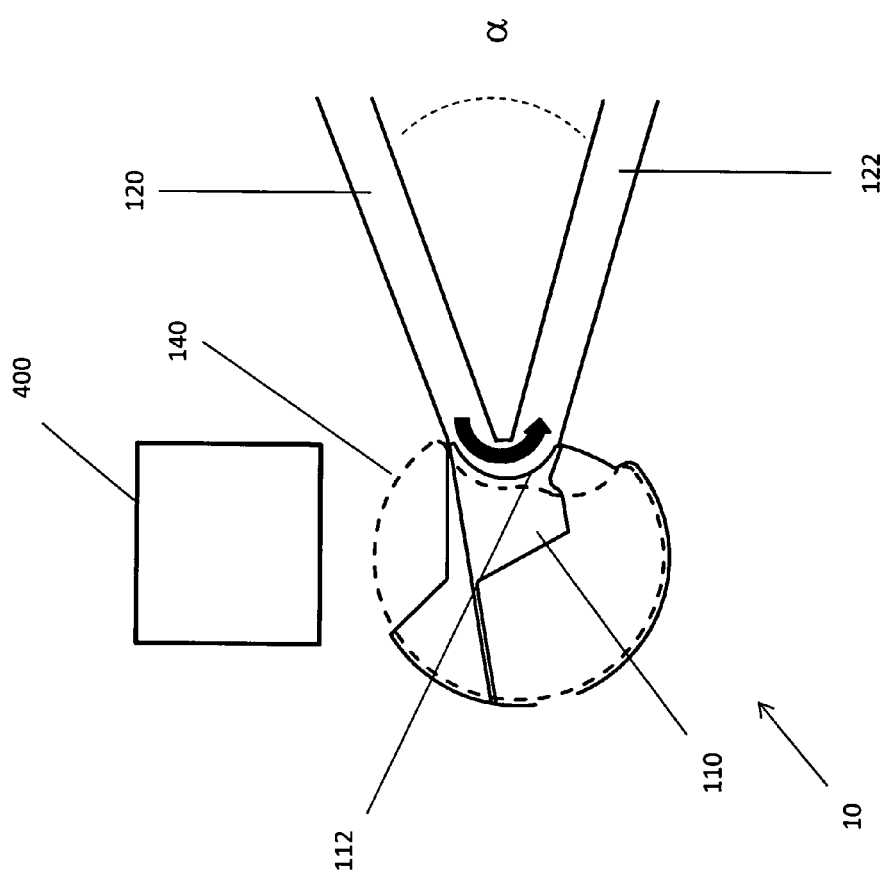
FIG. 2 is a simplified plan view of a microfabricated particle sorting system in the actuated (sort) position.

FIG. 2 is a plan view of the microfabricated device 10 in the actuated position. In this position, the movable member or valve 110 is deflected upward into the position shown in FIG. 2. The diverting surface 112 is a sorting contour which redirects the flow of the inlet channel 120 into the sort output channel 122. The output channel 122 may lie in substantially the same plane as the inlet channel 120, such that the flow within the sort channel 122 is also in substantially the same plane as the flow within the inlet channel 120. There may be an angle α between the inlet channel 120 and the sort channel 122. This angle may be any value up to about 90 degrees. Actuation of movable member 110 may arise from a force from force-generating apparatus 400, shown generically in FIG. 2. In some embodiments, force-generating apparatus may be an electromagnet, however, it should be understood that force-generating apparatus may also be electrostatic, piezoelectric, or some other means to exert a force on movable member 110, causing it to move from a first position (FIG. 1) to a second position (FIG. 2).

More generally, the micromechanical particle manipulation device shown in FIGS. 1 and 2 may be formed on a surface of a fabrication substrate, wherein the micromechanical particle manipulation device may include a microfabricated, movable member 110 having a first diverting surface 112, wherein the movable member 110 moves from a first position to a second position in response to a force applied to the movable member, wherein the motion is substantially in a plane parallel to the surface, a sample inlet channel 120 formed in the substrate and through which a fluid flows, the fluid including one or more target particles and non-target material, wherein the flow in the sample inlet channel is substantially parallel to the surface, and a plurality of output channels 122, 140 into which the microfabricated member diverts the fluid, and wherein the flow in at least one of the output channels 140 is not parallel to the plane, and wherein at least one output channel 140 is located directly below at least a portion of the movable member 110 over at least a portion of its motion.

In one embodiment, the diverting surface 112 may be nearly tangent to the input flow direction as well as the sort output flow direction, and the slope may vary smoothly between these tangent lines. In this embodiment, the moving mass of the stream has a momentum which is smoothly shifted from the input direction to the output direction, and thus if the target particles are biological cells, a minimum of force is delivered to the particles. As shown in FIGS. 1 and 2, the micromechanical particle manipulation device 10 has a first diverting surface 112 with a smoothly curved shape, wherein the surface which is substantially tangent to the direction of flow in the sample inlet channel at one point on the shape and substantially tangent to the direction of flow of a first output channel at a second point on the shape, wherein the first diverting surface diverts flow from the sample inlet channel into the first output channel when the movable member 110 is in the first position, and allows the flow into a second output channel in the second position.

In other embodiments, the overall shape of the diverter 112 may be circular, triangular, trapezoidal, parabolic, or v-shaped for example, but the diverter serves in all cases to direct the flow from the inlet channel to another channel.

It should be understood that although channel 122 is referred to as the "sort channel" and orifice 140 is referred to as the "waste orifice", these terms can be interchanged such that the sort stream is directed into the waste orifice 140 and the waste stream is directed into channel 122, without any loss of generality. Similarly, the "inlet channel" 120 and "sort channel" 122 may be reversed. The terms used to designate the three channels are arbitrary, but the inlet stream may be diverted by the valve 110 into either of two separate directions, at least one of which does not lie in the same plane as the other two. The term "substantially" when used in reference to an angular direction, i.e. substantially tangent or substantially vertical, should be understood to mean within 15 degrees of the referenced direction. For example, "substantially orthogonal" to a line should be understood to mean from about 75 degrees to about 105 degrees from the line.

Figure 3B:
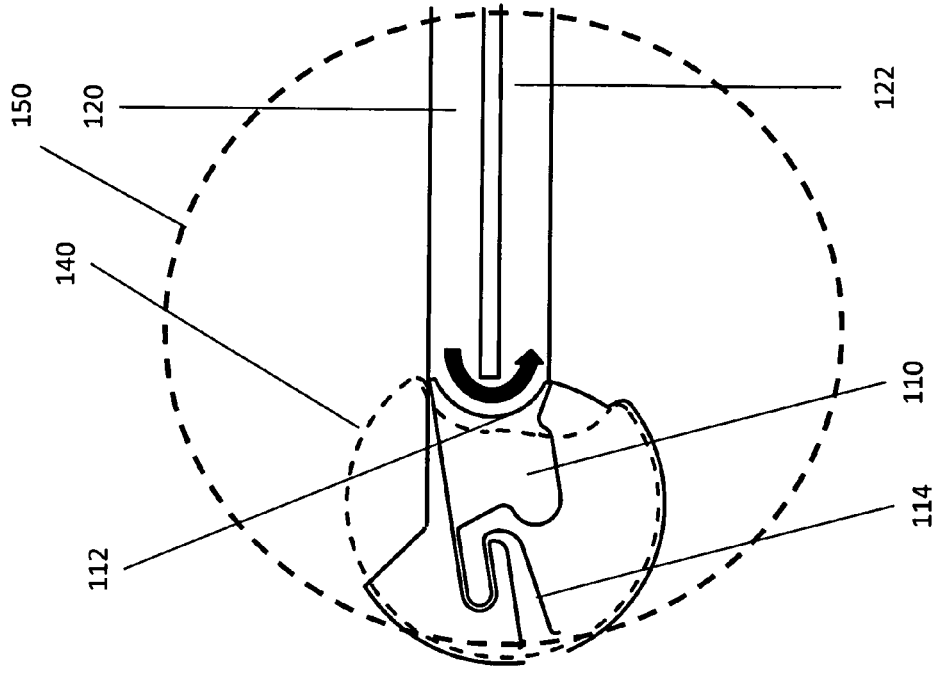
FIG. 3b is a simplified illustration of a microfabricated particle sorting system showing the field of view of the detector, with the microfluidic valve in the actuated (sort) position.
Figure 3A:
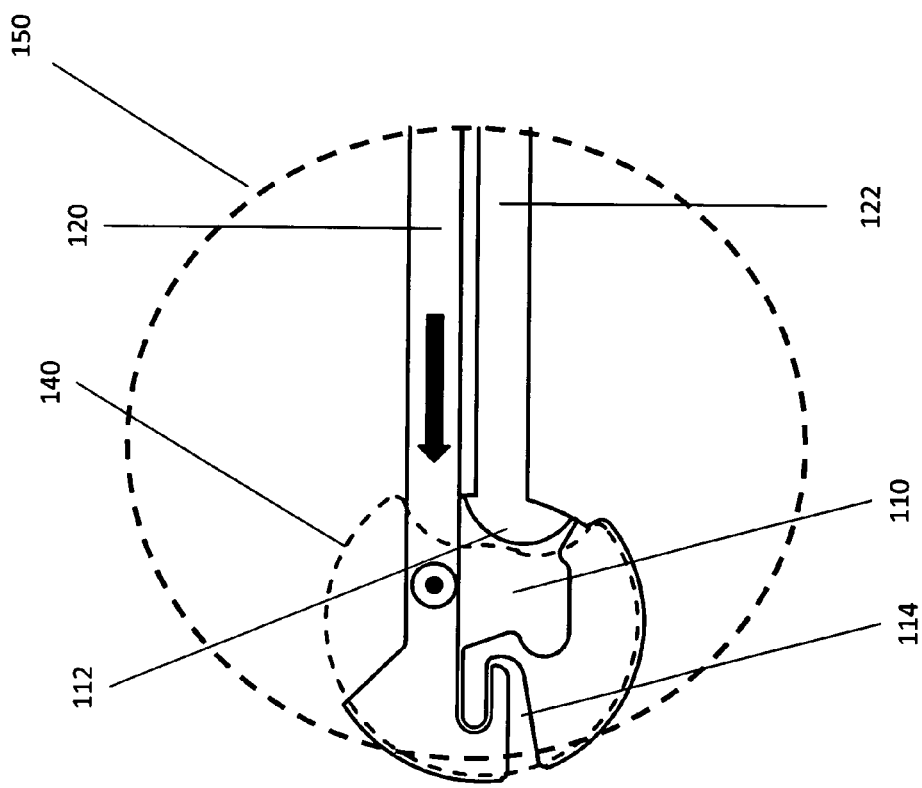
FIG. 3a is a simplified plan view of a microfabricated particle sorting system showing the field of view of the detector, with the microfluidic valve in the quiescent (no sort) position.

FIGS. 3a and 3b illustrate an embodiment wherein the angle a between the inlet channel 120 and the sort channel 122 is approximately zero degrees. Accordingly, the sort channel 122 is essentially antiparallel to the inlet channel 120, such that the flow is from right to left in the inlet channel 120. With valve 110 in the un-actuated, quiescent position shown in FIG. 3a, the inlet stream flows straight to the waste orifice 140 and vertically out of the device 10.

In FIG. 3b, the valve 110 is in the actuated, sort position. In this position, the flow is turned around by the diverting surface 112 of the valve 110 and into the antiparallel sort channel 122. This configuration may have an advantage in that the field of view of the detector 150 covers both the inlet channel 120 and the sort channel 122. Thus a single set of detection optics may be used to detect the passage of a target particle through the respective channels. It may also be advantageous to minimize the distance between the detection region and the valve 110, in order to minimize the timing uncertainty in the opening and closing of the valve.

The movable member or valve 110 may be attached to the substrate with a flexible spring 114. The spring may be a narrow isthmus of substrate material. In the example set forth above, the substrate material may be single crystal silicon, which is known for its outstanding mechanical properties, such as its strength, low residual stress and resistance to creep. With proper doping, the material can also be made to be sufficiently conductive so as to avoid charge build up on any portion of the device, which might otherwise interfere with its movement. The spring may have a serpentine shape as shown, having a width of about 1 micron to about 10 microns and a spring constant of between about 10 N/m and 100 N/m, and preferably about 40 N/m.

FIGS. 4a, 4b, 4c are cross sectional views illustrating the operation of the out-of-plane waste channel 140. FIG. 4c is slightly enlarged relative to FIGS. 4a and 4b, in order to show detail of the flow around the movable member 110 and into the waste channel 142 through waste orifice 140. In this embodiment, the waste channel 142 is vertical, substantially orthogonal to the inlet stream 120 and sort stream 122. It should be understood that other embodiments are possible other than orthogonal, but in any event, the flow into waste channel 142 is out of the plane of the flow in the inlet channel 120 and/or sort channel 122. As shown in FIG. 4a, with the valve in the sort, actuated position, the inlet stream and target particle may flow into the sort stream, which in FIG. 4a is out of the paper, and the waste orifice 140 is largely, though not completely, blocked by the movable member 110. The area 144 (shown more clearly in FIG. 4c) on top of the valve or movable member 110 may be relieved to provide clearance for this flow.

When the valve or movable member 110 is un-actuated as in FIG. 4b, the flow of the inlet channel 120 may flow directly into the waste channel 142 by going over, around or by the movable member or valve 110. The area 144 on top of the valve or movable member 110 may be relieved to provide clearance for this flow. The relieved area 144 is shown in greater detail in the enlarged FIG. 4c. Thus when the movable member is un-actuated, the flow will be sent directly to the waste channel. When the movable member is actuated, most of the fluid will be directed to the sort channel, although liquid may still flow over and under the movable member.

Thus, the purpose of providing flow both under and over the movable member 110 is to reduce the fluid pressure produced by the actuator motion in the region behind the valve or movable member 110. In other words, the purpose is to provide as short a path as possible between the high pressure region in front of the valve 110 and the low pressure region behind the valve. This allows the valve to operate with little pressure resisting its motion. As a result, the movable valve 110 shown in FIGS. 1-4c may be substantially faster than valves which have all channels disposed in the same plane.

Another advantage of the vertical waste channel 142 is that by positioning it directly underneath a stationary permeable feature 130 and movable permeable feature 116, the magnetic gap between the permeable features 116 and 130 can be narrower than if the fluidic channel went between them. The narrower gap enables higher forces and thus faster actuation compared to prior art designs. A description of the magnetic components and the magnetic actuation mechanism will be given next, and the advantages of the out-of-plane channel architecture will be apparent.

Figure 5:
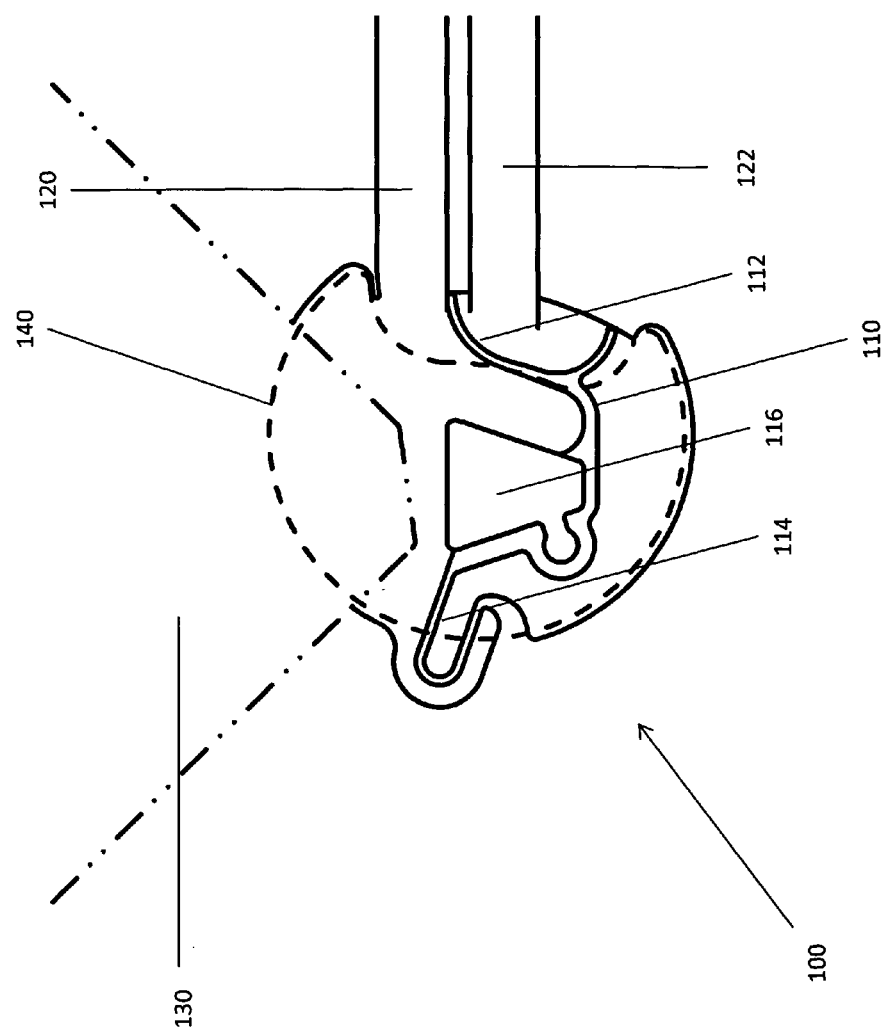
FIG. 5 is a simplified plan view of a microfabricated particle sorting system in the quiescent (no sort) position, showing the stationary magnetically permeable feature.

FIG. 5 is a plan view of another exemplary embodiment of device 100 of the device 10, showing the disposition of a stationary permeable feature 130 and further detail of the movable member 110. In this embodiment, the movable member 110 may include the diverting surface 112, the flexible hinge or spring 114, and a separate area 116 circumscribed but inside the line corresponding to movable member 110. This area 116 may be inlaid with a permeable magnetic material such as nickel-iron permalloy, and may function as described further below.

A magnetically permeable material should be understood to mean any material which is capable of supporting the formation of a magnetic field within itself In other words, the permeability of a material is the degree of magnetization that the material obtains in response to an applied magnetic field.

The terms "permeable material" or "material with high magnetic permeability" as used herein should be understood to be a material with a permeability which is large compared to the permeability of air or vacuum. That is, a permeable material or material with high magnetic permeability is a material with a relative permeability (compared to air or vacuum) of at least about 100, that is, 100 times the permeability of air or vacuum which is about $1.26 \times 10^{-6}$ H·m$^{-1}$. There are many examples of permeable materials, including chromium (Cr), cobalt (Co), nickel (Ni) and iron (Fe) alloys. One popular permeable material is known as Permalloy, which has a composition of between about 60% and about 90% Ni and 40% and 10% iron. The most common composition is 80% Ni and 20% Fe, which has a relative permeability of about 8,000.

It is well known from magnetostatics that permeable materials are drawn into areas wherein the lines of magnetic flux are concentrated, in order to lower the reluctance of the path provided by the permeable material to the flux. Accordingly, a gradient in the magnetic field urges the motion of the movable member 110 because of the presence of inlaid permeable material 116, towards areas having a high concentration of magnetic flux. That is, the movable member 110 with inlaid permeable material 116 will be drawn in the direction of positive gradient in magnetic flux.

Figure 6:
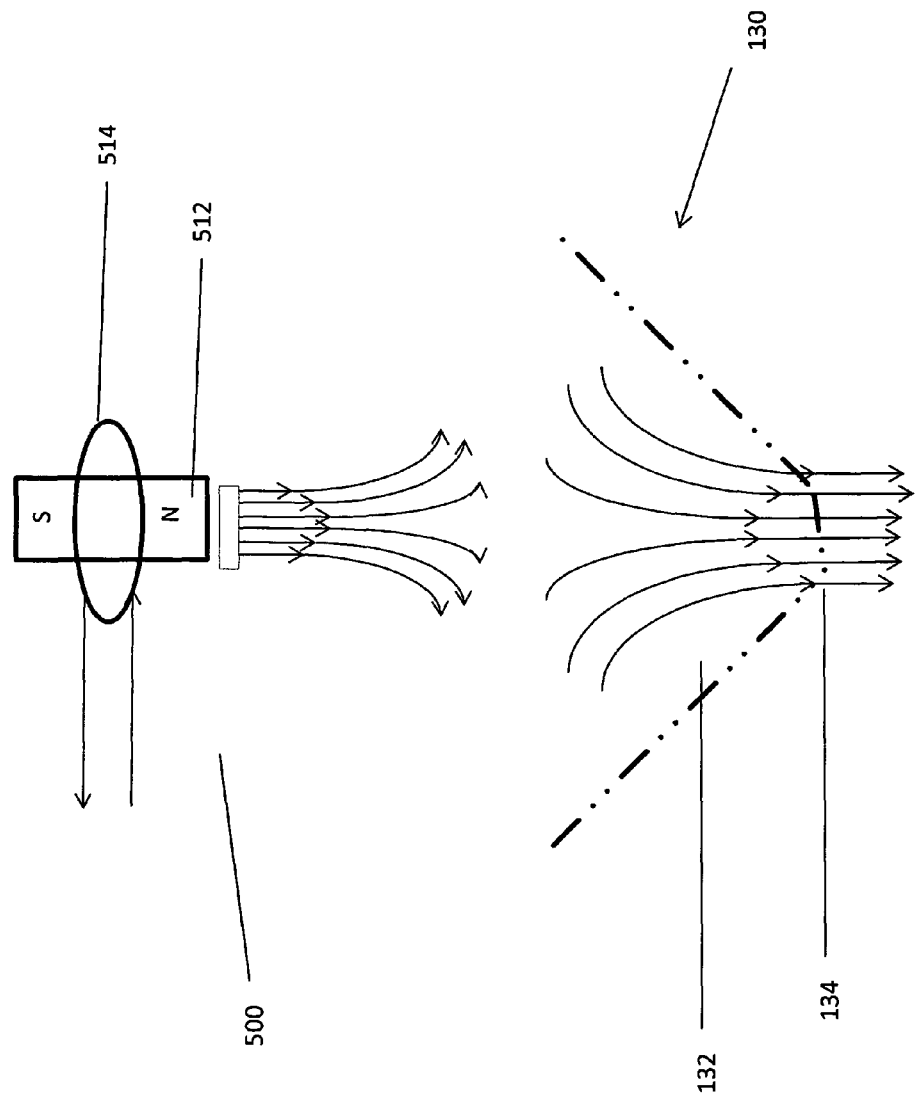
FIG. 6 is a plan view of the actuation mechanism for the microfabricated particle sorting system, showing the functioning of the external magnetic field in combination with the stationary magnetically permeable feature.
Figure 7:
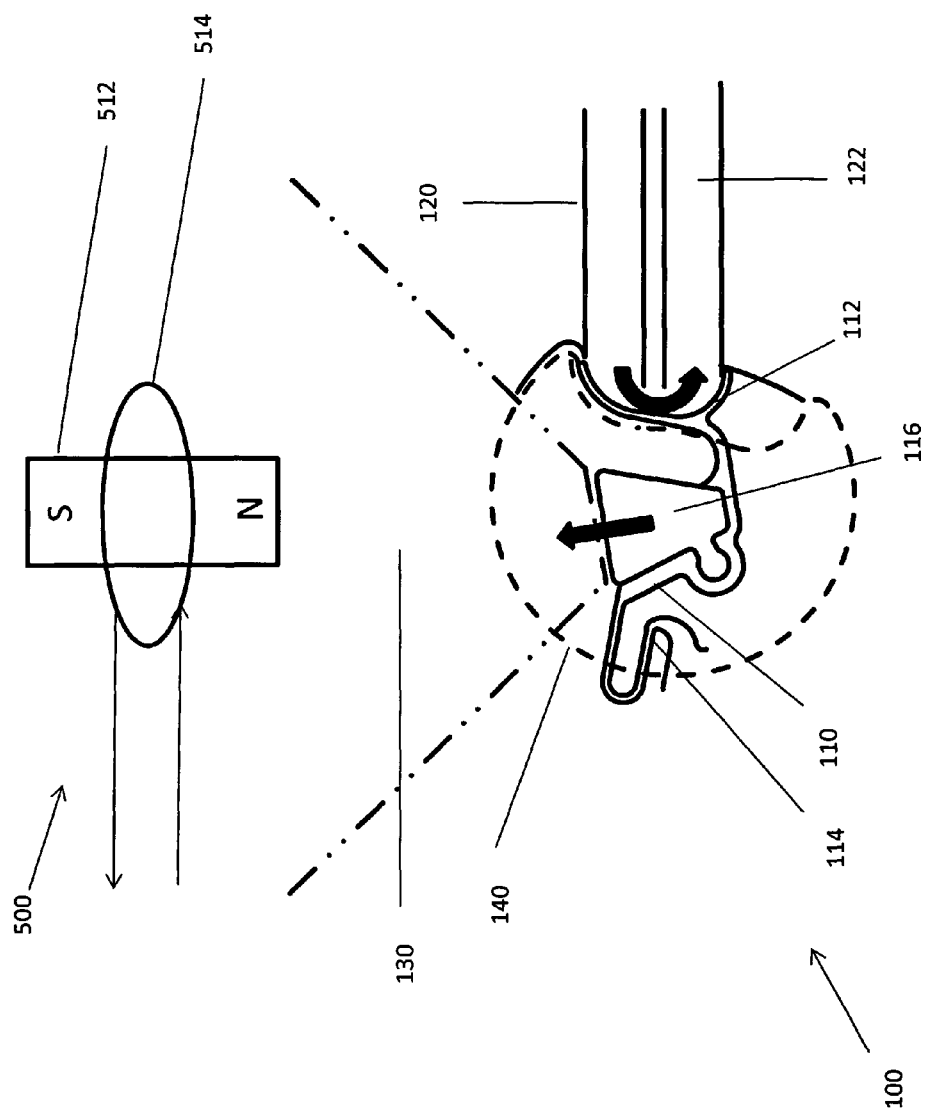
FIG. 7 is a plan view of the actuation mechanism for the microfabricated particle sorting system, showing the functioning of the external magnetic field in combination with the stationary magnetically permeable feature, in the actuated (sort) position.

An external source of magnetic field lines of flux may be provided outside the device 100, as shown in FIG. 6. This source may be an electromagnet 500. The electromagnet 500 may include a permeable core 512 around which a conductor 514 is wound. The wound conductor or coil 514 and core 512 generate a magnetic field which exits the pole of the magnet, diverges, and returns to the opposite pole, as is well known from electromagnetism. Accordingly, the movable member 110 is generally drawn toward the pole of the electromagnet 500 as shown in FIG. 7.

However, the performance of the device 100 can be improved by the use of a stationary permeable feature 130. The term "stationary feature" should be understood to mean a feature which is affixed to the substrate and does not move relative to the substrate, unlike movable member or valve 110. A stationary permeable feature 130 may be shaped to collect these diverging lines of flux and refocus them in an area directly adjacent to the movable member 110 with inlaid permeable material. The stationary permeable feature may have an expansive region 132 with a narrower throat 134. The lines of flux are collected in the expansive region 132 and focused into and out of the narrow throat area 134. Accordingly, the density of flux lines in the throat area 134 is substantially higher than it would be in the absence of the stationary permeable feature 130. Thus, use of the stationary permeable feature 130 though optional, allows a higher force, faster actuation, and reduces the need for the electromagnet 500 to be in close proximity to the device 10. From the narrow throat area 134, the field lines exit the permeable material and return to the opposite magnetic pole of the external source 500. But because of the high concentration of field lines in throat area 134, the permeable material 116 inlaid into movable member 110 may be drawn toward the stationary permeable feature 130, bringing the rest of movable member with it.

When the electromagnet is quiescent, and no current is being supplied to coil 514, the restoring force of spring 114 causes the movable member 110 to be in the "closed" or "waste" position. In this position, the inlet stream passes unimpeded through the device 100 to the waste channel 140. This position is shown in FIG. 5. When the electromagnet 500 is activated, and a current is applied through coil 514, a magnetic field arises in the core 512 and exits the pole of the core 512. These lines of flux are collected and focused by the stationary permeable feature 130 and focused in the region directly adjacent to the throat 134. As mentioned previously, the permeable portion 116 of the movable member 110 is drawn toward the throat 134, thus moving the movable member 110 and diverting surface 112 such that the inlet stream in inlet channel 120 is redirected to the output or sort channel 122. This position is shown in FIG. 7.

Permalloy may be used to create the permeable features 116 and 130, although it should be understood that other permeable materials may also be used. Permalloy is a well known material that lends itself to MEMS lithographic fabrication techniques. A method for making the permeable features 116 and 130 is described further below.

As mentioned previously, having the waste channel 140 and 142 directly beneath the movable member or valve 110 allows the movable permeable feature 116 to be disposed much closer to the stationary permeable feature 130. If instead the waste channel were in the same plane, this gap would have to be at least large enough to accommodate the waste channel, along with associated tolerances. As a result, actuation forces are higher and valve opening and closing times are much shorter. This in turn corresponds to either faster sorting or better sorting accuracy, or both.

With the use of the electromagnetic actuation technique described above, actuation times on the order of 10 microseconds can be realized. Accordingly, the particle sorting device is capable of sorting particles at rates in excess of 50 kHz or higher, assuming 10 microseconds required to pull the actuator in, and 10 microseconds required to return it to the as-manufactured position.

For any particle sorting mechanism however, there is an inherent trade-off between sort purity and sort speed. One can only increase the fluid speed to a certain point, after which one runs into physical limitations of the sorter, for example, when the valve speed is such that there is insufficient time to open the valve or flap when a cell is detected. Beyond that limitation, the most obvious way to achieve more events per second is to increase the cell density. But, with increased cell density, the incidence of sort conflicts, wherein both a desired and an undesired cell are collected, also increases.

In order to overcome this limitation, a cell sample may theoretically be processed multiple times in a sequential sort strategy—initially a very rapid, crude sort followed by a—slower, high precision sort. This is generally not a practical option with a traditional FACS system as a result of massive cell dilution (from sheath fluid), slow processing speeds and unacceptable cell damage resulting from multiple passes through the high pressure electrostatic sorting mechanism. A single pass through a flow cytometer is exceptionally violent, with 10 msec velocities, explosive decompression from 60 psi to 0 psi. Cells are unlikely to survive such treatment on multiple passes without significant loss of viability. Even if one is willing to accept the dilution, manual processing and cell death, the yield losses on a FACS would be overwhelming. Also, the time constant per cycle for processing, cleaning, sterilization and certification is untenable and the sterility of the sample is completely compromised. As a result, this sequential sorting is not a practical approach for FACS-based clinical cell sorting.

In contrast, for the microfabricated particle sorting system described above, using the microfluidic channel architecture, a multi-stage, "sequential" sort may be performed in a straightforward way as described below. A plurality of particle manipulation operations may take place using a plurality of MEMS sorting devices 10 or 100. The sorting devices may be on separate MEMS chips and enclosed in a disposable cartridge, or multiple valves may be formed on a single substrate using MEMS fabrication techniques. In one embodiment, the plurality of MEMS sorting chips are separated by some extent, such that by laterally shifting the device, the additional MEMS chips may become operational. This embodiment is described further below, and illustrated in FIG. 8. More broadly, the sorting device system may include a secondary manipulation device or sorting stage 200 downstream of the first manipulation device or sorting stage 100. Sorting stage 100 connotes a stage using either device 10 or device 100 for example, as illustrated in FIGS. 1 and 5, respectively.

Figure 12:
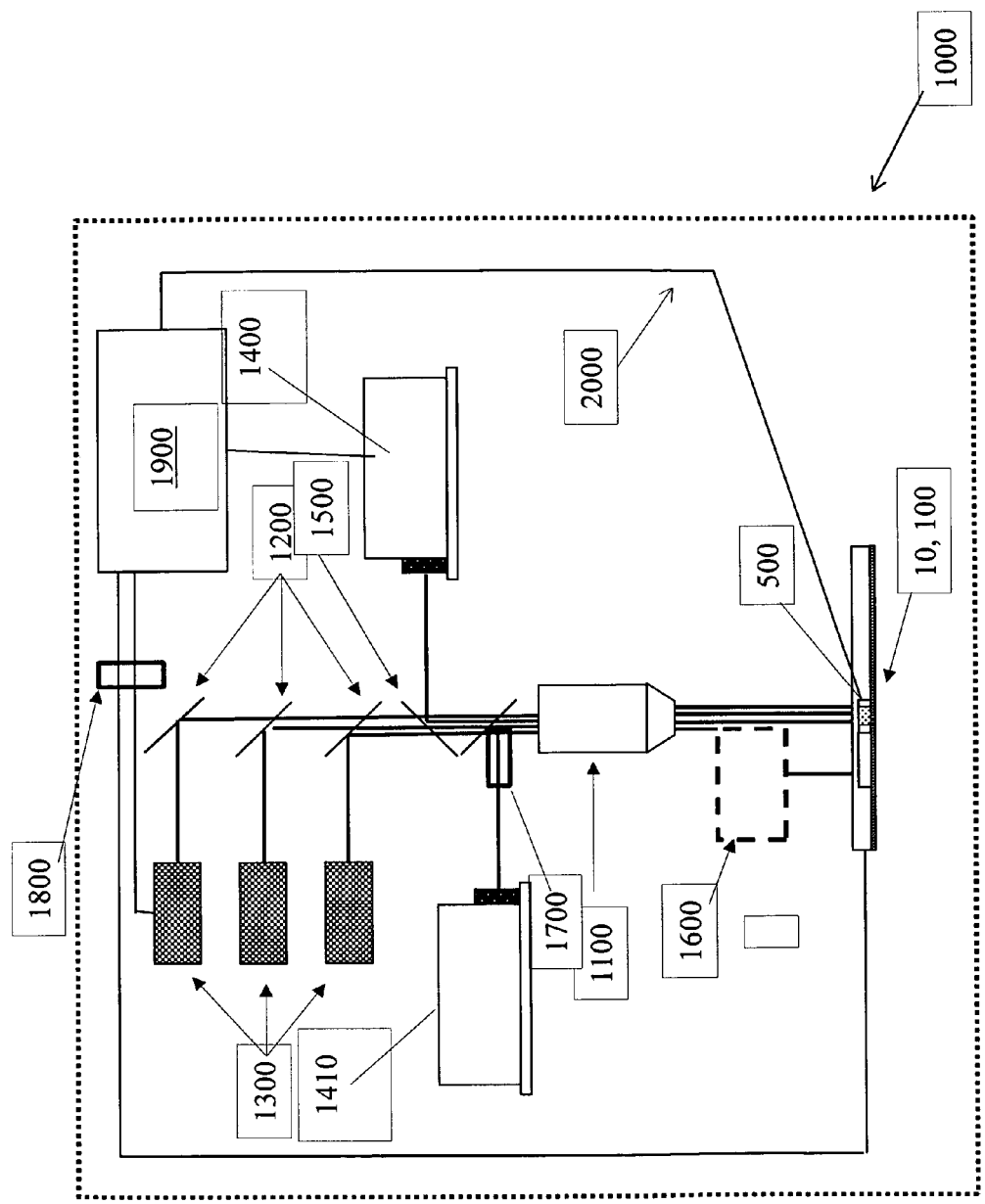
FIG. 12 is a system-level illustration of a microfabricated particle sorting system according to the present invention, showing the placement of the various detection and control components.

The first sorting stage 100 and second sorting stage 200 are both preceded by a laser interrogation region 170 and 270, respectively. In this region, a laser is used to irradiate the particles in the sample stream. Those particles bearing a fluorescent tag may fluoresce as a result of the laser irradiation. This fluorescence signal is detected and is indicative of the presence of a target particle in the sample stream. Upon detection of the target particle, a signal is sent to the controller controlling the electromagnet 500, energizing the electromagnet and thus opening the movable member or valve 110. The target particle is thus directed into the sort channel 122. This functionality is described in further detail below with respect to the full particle sorting system shown in FIG. 12. The sorting stages 100 and 200 may also be accompanied by a third laser interrogation region 280 downstream of the last sorting stage 200. This interrogation may be performed to evaluate the accuracy of the sort, or in order to adjust various sorting parameters. Although only two sorting operations arranged sequentially are shown in FIG. 12, it should be understood that this basic concept may be extended to any number of additional sorting stages, and that the stages may be arranged in a parallel configuration, instead of, or in addition to, the serial configuration.

Figure 8:
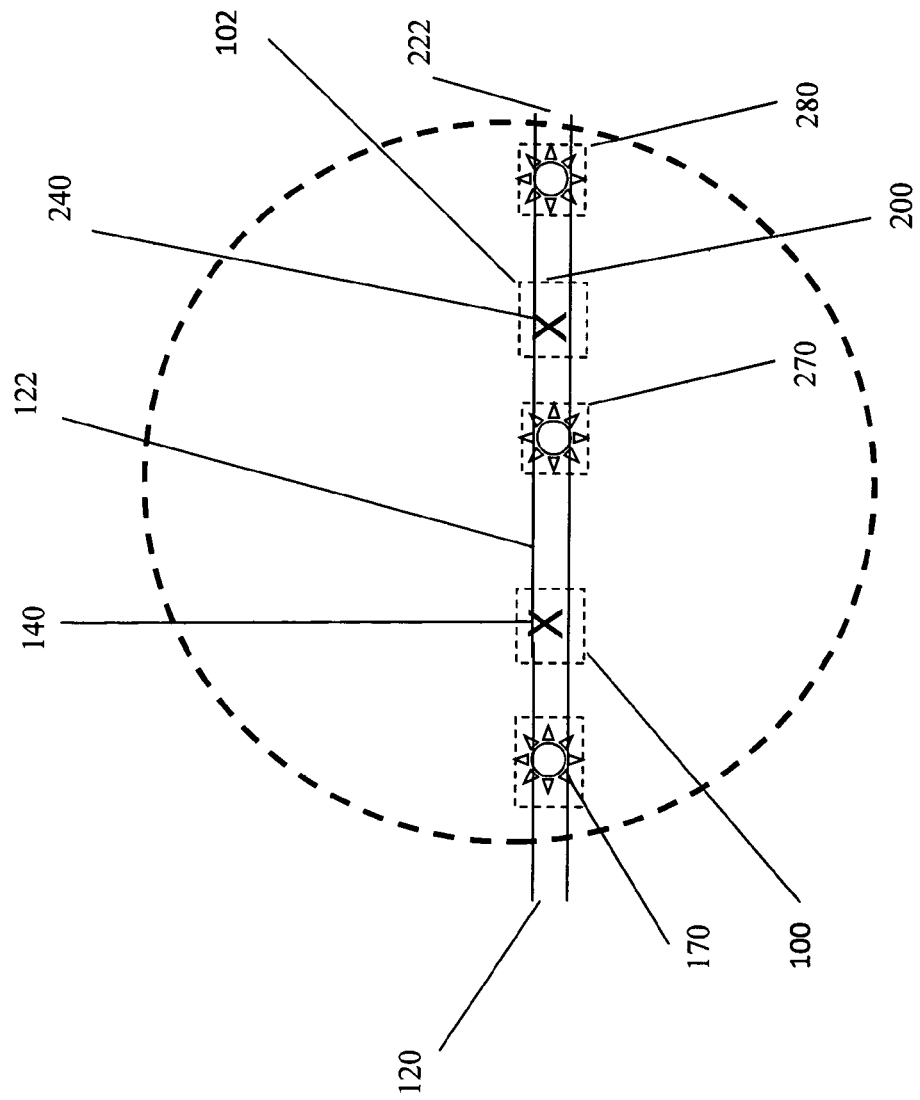
FIG. 8 is a simplified view of the microfabricated particle sorting system, wherein multiple microfabricated particle sorters are arranged to provide a serial sorting capability.

Accordingly, a first sort may be run rapidly through a first sorting stage 100, to enrich target cells with negligible yield losses. The output of the first sorting stage 100 may flow into either a waste channel 140 or a sort channel 122, based on the output of a discriminator or detector located in region 170. If the stream flows to the sort channel 122, it then flows on to a second sorting stage 200, which may have its own associated detection area 270. Similarly to sort stage 100, the flow may be direct to a waste channel 240 or a sort channel 222. Using this approach, the sample remains sterile and gently handled through the entire sequential sorting process. It should be understood that although difficult to depict in a two dimensional drawing, the waste channel 140 and 240 may lie in a different plane relative to the inlet channel 120, and sort channels 122 and 222. In FIG. 8 waste channels 140 and 240 are depicted flowing into the paper.

Figure 9:
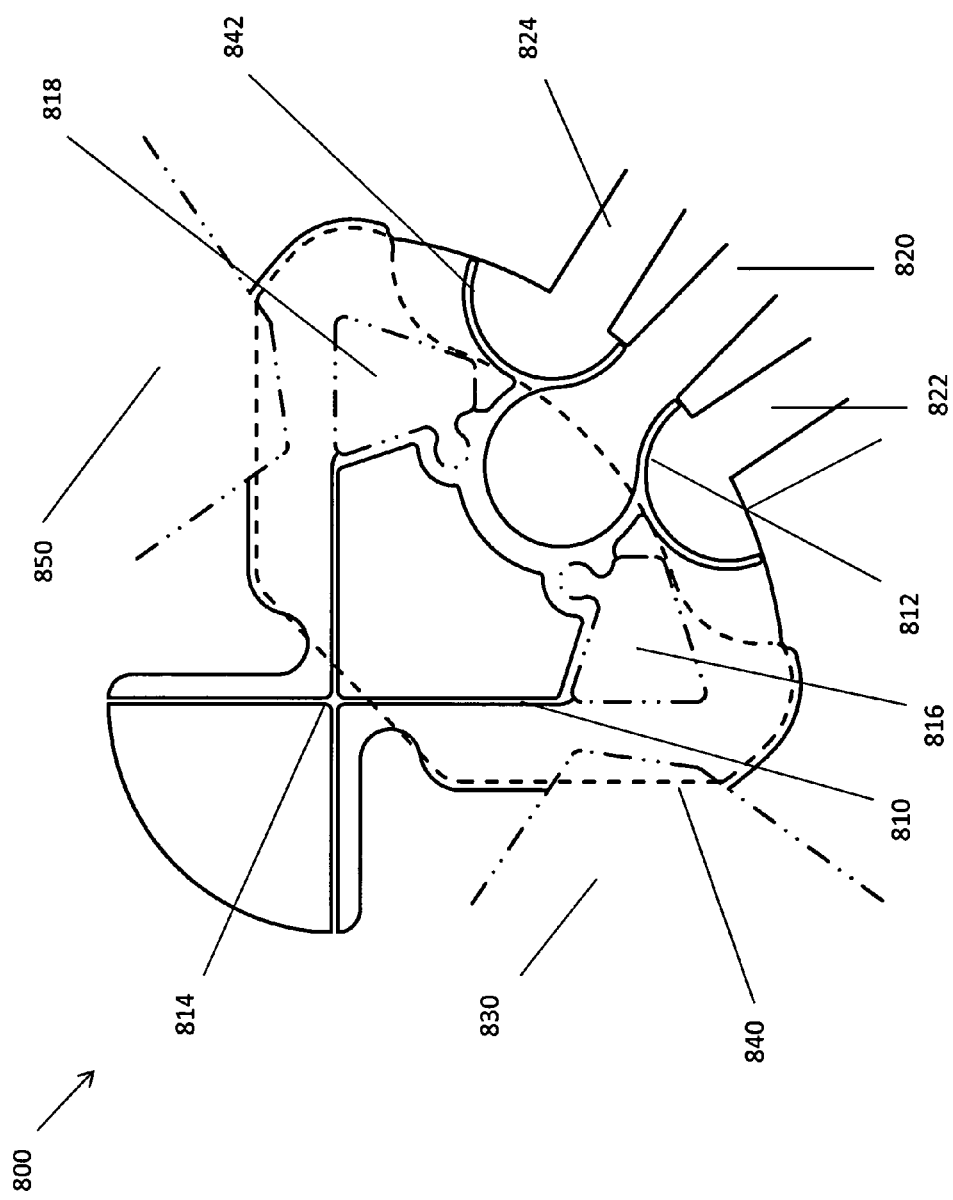
FIG. 9 is a plan view of a two-way microfabricated particle sorting system, wherein the system has more than one sort output.
Figure 10:
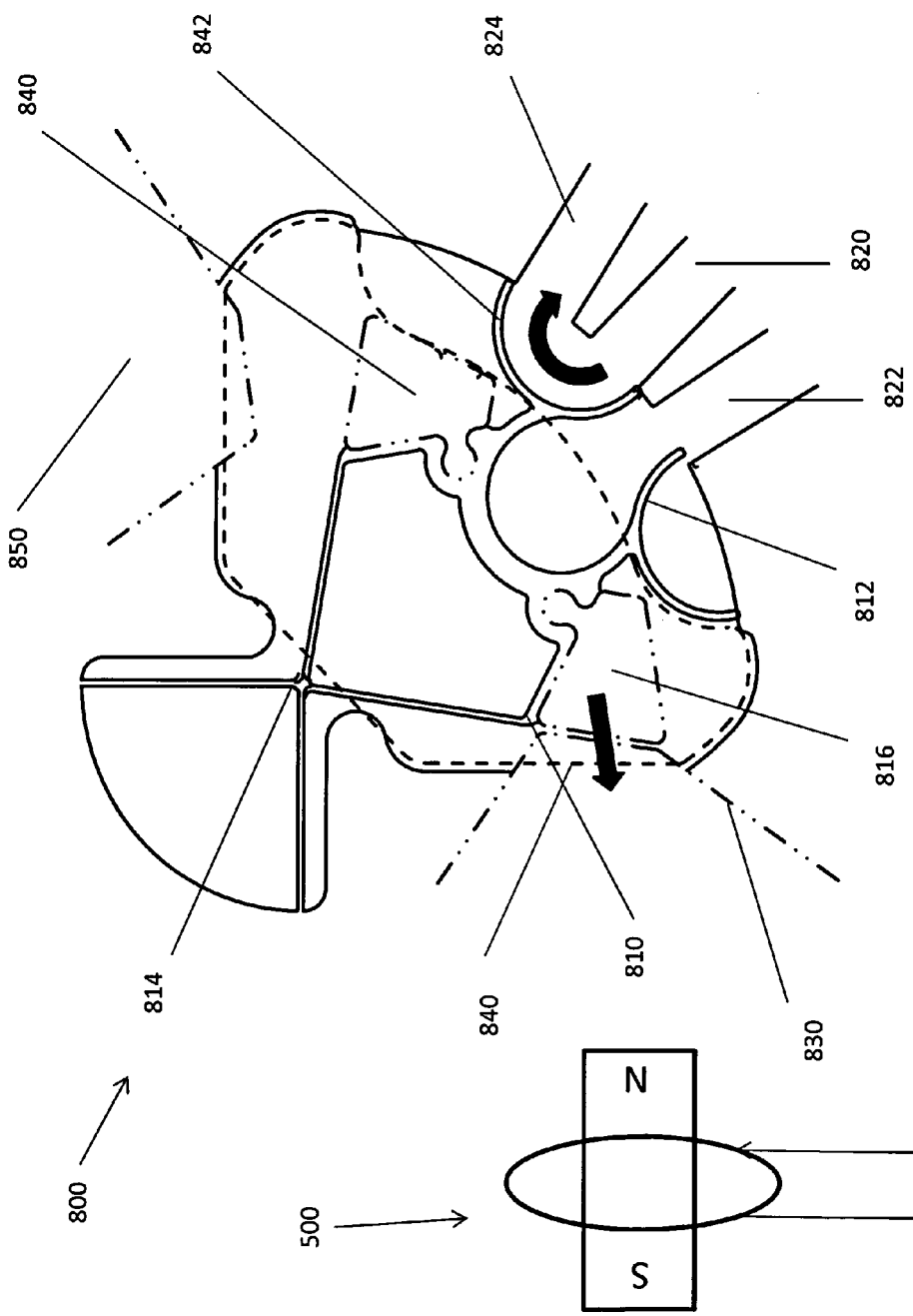
FIG. 10 is a plan view of the a two-way microfabricated particle sorting system, with more than one sort output, with the two-way microfabricated particle sorting device in the actuated position.

In another embodiment, using the architecture shown in FIG. 1, 3, or 5, a dual output, dual position particle manipulation device may also be envisioned. Such a device is shown in FIG. 9. FIG. 9 shows a dual output device 800 wherein a single inlet channel 820 can feed either of two separate sort output channels 822 and 824, depending on the position of movable member 810. Dual output device 800 may have two permeable areas 816 and 818, which may be drawn toward either of two stationary permeable features 830 and 850, respectively. For example, if a source of external magnetic flux such as electromagnet 500 is positioned near stationary permeable feature 830, the flux emitted from electromagnet 500 is concentrated by stationary permeable feature 830 and movable permeable feature 816 is drawn toward it. The situation is as depicted in FIG. 10. When the movable feature rotates clockwise, opening sort channel 822 to the flow from inlet channel 820 by diverting surface 842. When another external magnet (not shown) is energized above device 800 and upper stationary permeable feature 850, the movable member 810 rotates counterclockwise, directing the flow in inlet channel 820 into the upper sort channel 824 by sort diverting surface 812. The waste channel orifice 840 may be enlarged compared to 140, such that it is disposed directly under at least a portion of movable member 810, but does not interfere with the motion of sort diverting surfaces 812 or 842.

Although the embodiments shown in FIGS. 1-11 are described with respect to an electromagnetic actuation mechanism, it should be understood that other actuation forces may be used instead. For example, if permeable features 116 and 130 are made from an electrically conductive rather than permeable magnetic material, a voltage potential may be placed across elements 116 and 130, producing an electrostatic force to move the movable member 110. Piezoelectric forces may also be used.

Figure 11:
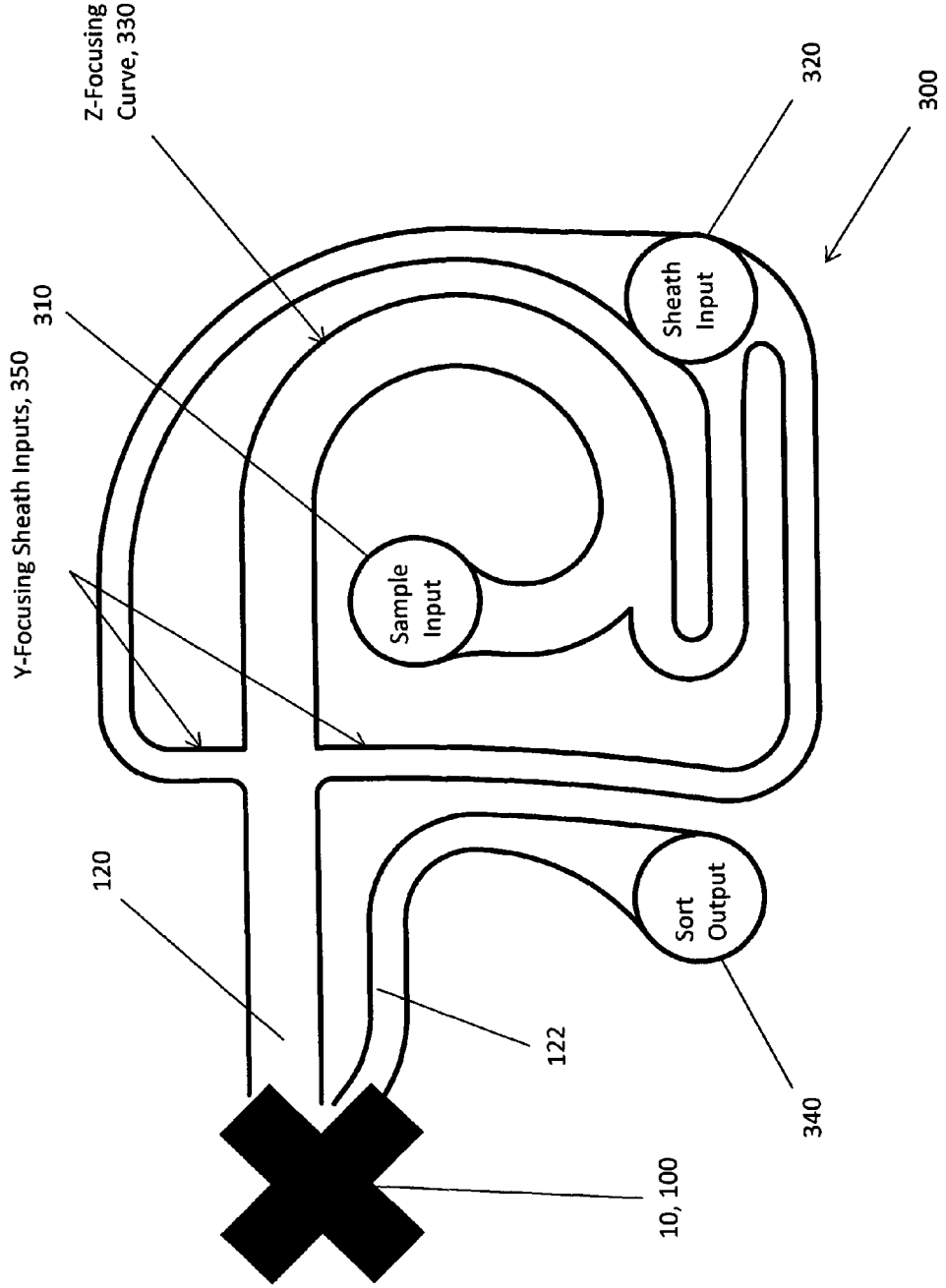
FIG. 11 is a plan view of the microfabricated particle sorting system in combination with a hydrodynamic focusing manifold.

Because of the microfabricated architecture of particle manipulation device 10 and 100, it lends itself to techniques that can make use of such an enclosed, well defined architecture. One such technique is illustrated in FIG. 11, wherein the microfabricated particle manipulation device may have at least one additional channel that provides a sheath fluid to the sample stream and also a focusing element coupled to the inlet channel. The sheath fluid may be used to adjust the concentration or positioning of the target particles within the inlet channel. The focusing element may be configured to urge the target particles into a particular portion of the sample inlet channel, as described further below. The focusing element may be disposed in substantially the same plane as the movable member 110, and may be formed in the same substrate surface as the movable member 110 and inlet channel 120.

FIG. 11 depicts a microfabricated fluidic manifold 300 which may be used to focus the particles in a certain area within the fluid stream. Techniques for designing such a manifold may be found in, for example, "Single-layer planar on-chip flow cytometer using microfluidic drifting based three-dimensional (3D) hydrodynamic focusing," by Xiaole Mao et cl, Journal of Royal Society of Chemistry, Lab Chip, 2009, 9, 1583-1589. The manifold may include a sample inlet 310 and sheath fluid channel 320. As the name suggests, the sheath channel adds a sheath fluid to the sample stream, which is a buffering fluid which tends to dilute the flow of particles in the stream and locate them in a particular portion of the stream. The combined fluid then flows around a focusing element coupled to the inlet channel 120, here a z-focusing channel 330, which tends to herd the particles into a particular plane within the flow. This plane is substantially in the plane of the paper of FIG. 11. The combined fluid then passes another intersection point, a "y-intersection point" 350, which introduces additional sheath fluid above and below the plane of particles. At the y-intersection point 350, two flows may join the z-focus channel 330 from substantially antiparallel directions, and orthogonal to the z-focus channel 330. This intersection may compress the plane of particles into a single point, substantially in the center of the stream. Accordingly, at the y-intersection point 350 the target particles may be compressed from a plane to a stream line near the center of the z-focus channel 330 and sample inlet channel 120. Focusing the particles into a certain volume tends to decrease the uncertainly in their location, and thus the uncertainty in the timing of the opening and closing of the movable member or valve 110. Such hydrodynamic focusing may therefore improve the speed and/or accuracy of the sorting operation.

In one exemplary embodiment of the microfabricated particle manipulation device 10 or 100 with hydrodynamic focusing illustrated in FIG. 11, the angular sweep of z-bend 330 is a curved arc of about 180 degrees. That is, the approximate angular sweep between the junction of the sheath inlet with the cell inlet and the y-intersection point 350, may be about 180 degrees. Generally, the radius of curvature of the z-bend 330 may be at least about 100 microns and less than about 500 microns, and the characteristic dimension, that is the width, of the channels is typically about 50 microns to provide the focusing effect. In one embodiment, the radius of curvature of the channel may be about 250 microns, and the channel widths, or characteristic dimensioms, for the sample inlet channel 120 and z-bend channel are on the order of about 50 microns. These characteristic dimensions may provide a curvature sufficient to focus the particles, such that they tend to be confined to the plane of the paper upon exit from the z-focus channel 330 at y-intersection point 350. This plane is then compressed to a point in the channel at the y-intersection point 350.

The microfabricated particle manipulation device 10 or 100 may be used in a particle sorting system 1000 enclosed in a housing containing the components shown in FIG. 12. The MEMS particle manipulation devices 10, 100 or 800 may be enclosed in a plastic, disposable cartridge which is inserted into the system 1000. The insertion area may be a movable stage with mechanisms available for fine positioning of the particle manipulation device 10, 100 or 800 and associated microfluidic channels against one or more data, which orient and position the detection region and particle manipulation device 10, 100 or 800 with respect to the collection optics 1100. If finer positioning is required, the inlet stage may also be a translation stage, which adjusts the positioning based on observation of the location of the movable member 110 relative to a datum.

It should be understood that although FIG. 12 shows a particle sorting system 1000 which uses a plurality of laser sources 1400 and 1410, only a single laser may be required depending on the application. For the plurality of lasers shown in FIG. 12, one of the laser sources 1410 may be used with an associated set of parallel optics (not shown in FIG. 12) to illuminate the at least one additional laser interrogation region 170 and/or 270. This setup may be somewhat more complicated and expensive to arrange than a single laser system, but may have advantages in that the optical and detection paths may be separated for the different laser interrogation regions. For this embodiment, it may not be necessary to alter the trajectory, spectral content, timing or duration of the laser 1410 light. Although not shown explicitly in FIG. 12, it should be understood that the detection path for additional laser(s) 1410 may also be separate from the detection path for laser 1400. Accordingly, some embodiments of the particle sorting system may include a plurality of laser sources and a plurality of optical detection paths, whereas other embodiments may only use a single laser source 1400 and collection optics 1100. In the embodiment described here, a plurality of excitation lasers uses a common optical path, and the optical signals are separated electronically by the system shown in FIG. 12.

The embodiment shown in FIG. 12 is based on a FACS-type detection mechanism, wherein one or more lasers 1400, 1410 excites one or more fluorescent tags affixed to the target particles. The laser excitation may take place in multiple interrogation regions, such as regions 170, 270 and 280. The fluorescence emitted as a result are detected and the signal is fed to a computer 1900. The computer then generates a control signal that controls the electromagnet 500, or multiple electromagnets if multiple sorters are used such as in FIG. 8. It should be understood that other detection mechanisms may be used instead, including electrical, mechanical, chemical, or other effects that can distinguish target particles from non-target particles.

Accordingly, the MEMS particle sorting system 1000 shown in FIG. 12 may include a number of elements that may be helpful in implementing the additional interrogation regions 170 and 270, or more. First, an optical manipulating means 1600 may alter the trajectory, spectral content, timing or duration of the laser radiation from laser 1400 to the second or third interrogation spots. Examples of items that may be included in optical manipulating means 1600 are a birefringent crystal, spinning prism, mirror, saturable absorber, acousto-optic modulator, harmonic crystal, Q-switch, for example. More generally, optical manipulating means 1600 may include one or more items that alter laser frequency, amplitude, timing or trajectory along one branch of the optical path to an additional interrogation region.

For example, optical manipulating means 1600 may include a beamsplitter and/or acousto-optic modulator. The beam splitter may separate a portion of the incoming laser beam into a secondary branch or arm, where this secondary branch or arm passes through the modulator which modulates the amplitude of the secondary beam at a high frequency. The modulation frequency may be, for example, about 2 MHz or higher. The light impinging on the first laser interrogation region 101 may, in contrast, be continuous wave (unmodulated). The secondary branch or arm is then directed to the additional laser interrogation region 170 or 270. This excitation will then produce a corresponding fluorescent pattern from an appropriately tagged cell.

This modulated fluorescent pattern may then be picked up by the detection optics 1600, which may recombine the detected fluorescence from interrogation region 170 and/or 270 with fluorescence from laser interrogation region 170. The combined radiation may then impinge on the one or more detectors 1300.

An additional optical component 1700 may also alter the frequency, amplitude, timing or trajectory of the second beam path, however, it may perform this operation upstream (on the detector side) of the collection optics 1100 rather than downstream (on the sample side) of it, as does optical component 1600.

The output of detectors 1300 may be analyzed to separate the content corresponding to laser interrogation region 280 from the content corresponding to laser interrogation region 170 or 270. This may be accomplished by applying some electronic distinguishing means to the signals from detectors 1300. The details of electronic distinguishing means 1800 may depend on the choice for optical manipulation means 1600. For example, the distinguishing means 1800 may include a high pass stage and a low pass stage that is consistent with a photoacoustic modulator that was included in optical manipulating means 1600. Or electronic distinguishing means 1800 may include a filter (high pass and/or low pass) and/or an envelope detector, for example.

Therefore, depending on the choice of optical manipulating means 1600, the unfiltered signal output from detectors 1300 may include a continuous wave, low frequency portion and a modulated, high frequency portion. After filtering through the high pass filter stage, the signal may have substantially only the high frequency portion, and after the low pass stage, only the low frequency portion. These signals may then be easily separated in the logic circuits of computer 1900. Alternatively, the high pass filter may be an envelope detector, which puts out a signal corresponding to the envelop of the amplitudes of the high frequency pulses.

Other sorts of components may be included in electronic distinguishing means 1800 to separate the signals. These components may include, for example, a signal filter, mixer, phase locked loop, multiplexer, trigger, or any other similar device that can separate or distinguish the signals. Component 1800 may also include the high pass and/or low pass electronic filter or the envelope detector described previously. The two sets of signals from the electronic distinguishing means 1800 may be handled differently by the logic circuits 1900 in order to separate the signals.

Thus, a MEMS particle manipulation system may be used in conjunction with one or more additional downstream laser interrogation regions, wherein the additional laser interrogation regions are used to confirm the effectiveness or accuracy of a manipulation stage in manipulating a stream of particles. The downstream evaluation from laser interrogation region 280 past the sorting stage 100 and 200 may allow the operator to measure one event number (e.g. the captured event rate post-sort) divided by another event number (e.g. the initial event rate pre-sort) for individual particle types, and to feedback to adjust initial interrogation parameters (e.g. such as x, y, z position and also "open window" length in time) based on this ratio. This method may be used to optimize the yield or accuracy of the system 1000. Alternatively, the operator could measure the event rate post-sort of target cells, divided by total event rate post-sort feedback to adjust initial laser interrogation parameters such as x, y, z position and also "open window" length in time, in order to optimize the purity of the sorting system 1000. These sorting parameters may be adjusted by changing control signal 2000 which is sent by computer 1900 to electromagnet 500, or by changing the optical detection parameters or by changing the laser control signals, as shown in FIG. 12.

Figure 13:
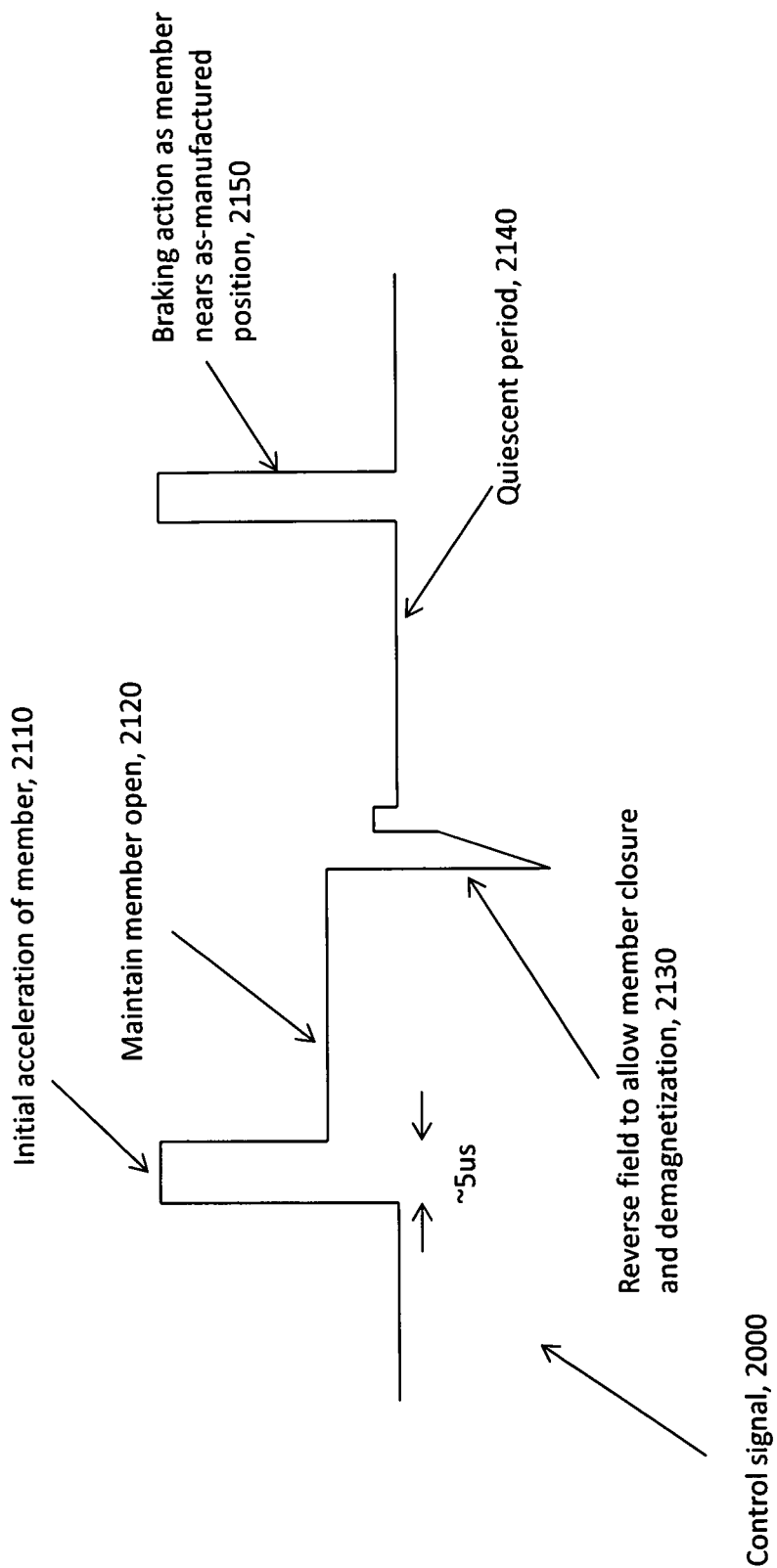
FIG. 13 is a representation of a signal waveform from the control system to the microfabricated particle sorting device, showing the different in pulses used to control the motion of the device.

One example of how the system depicted in FIG. 12 may be used to adjust the sorting parameters, is via the control signal waveform 2000 delivered to the electromagnet 500. This waveform 2000 may be fine-tuned to adjust the sorting performance of the valve or movable member 110 or 810, and may be produced by logic circuits 1900. FIG. 13 depicts a control signal waveform 2000 with additional features that may be used to control the motion of movable member 110 or 810. This control signal waveform 2000 may be generated by computer 1900, and thus may be made essentially arbitrarily complex. The control signal waveform 2000 may be either a voltage waveform or a current waveform. The control signal waveform 2000 may be applied to coil 510 of electromagnet 500, for example, to drive current through the coil to produce the actuating magnetic field. The control signal 2000 may include an acceleration phase 2110 which has a substantially larger magnitude than the remainder of the control signal waveform 2000, and lasts for tens of microseconds.

The larger magnitude of the current in the acceleration phase may be used to overcome the back electromotive force produced in the coils by the moving magnets. It may also produce a higher force, which may be needed to break the movable member 110, 810 from its rest position and overcome any stiction forces that may be hindering motion. After this initial acceleration phase, the control signal may have a maintenance phase during which the current is essentially constant and lasts for tens of microseconds. During this period, the movable member 110 or 810 travels from its closed position in FIG. 1, 5 or 9 to actuated positions shown in FIG. 2, 7 or 10. Although the current may be constant during this period, the force on the movable member may be variable, a function of the closing distance between movable permeable feature 116, 816 and 840 and the respective stationary permeable features 130, 840 and 850. Reversing the polarity of the control signal as shown in 2130 reverses the direction of the magnetic field, and demagnetizes the permeable portions. After the reversal period 2130, a quiescent period 2140 lasting several microseconds may follow, during which there is no magnetic field produced, and the spring force of spring element 114 or 814 on movable member 110 or 810 may return the movable member to its un-actuated state. This may be in the waste or reject position. After a period when the actuator is closing and about to reach the as-manufactured position, a short "braking" pulse 2150 may slow the velocity of the movable member. This may avoid an undesirable bounce off the hard stop, which may otherwise allow a non-target particle to enter the sort channel 122. Or if there is no hard stop, this may allow the fastest return to the un-actuated position.

Using the downstream confirmation of the sort channel contents as described above with respect to FIG. 12, any of the adjustable parameters of the current profile shown in FIG. 13, such as amplitude and duration of the acceleration phase, amplitude and duration of the opening phase, duration of the quiescent phase, or amplitude and duration of the braking phase, may be adjusted to improve the sort performance of the system.

The description now turns to the fabrication of the devices shown in FIGS. 1-11. Fabrication may begin with the inlaid permeable features 116 and 130 formed in a first substrate. The substrate may be a single crystal silicon substrate, for example. To form these structures, depressions may be formed in these areas of the substrate surface by etching. First, photoresist may be deposited over the substrate surface and removed over the areas corresponding to 116 and 130. Then, the trenches may be formed by, for example, etching the substrate in potassium hydroxide (KOH) to form a suitable depression. A seed layer may be deposited conformally over the first substrate surface and patterned to provide the seed layer for plating NiFe into the trenches. The seed layer may be, for example, Ti/W or Cr/Au may then be deposited by sputtering, CVD or plasma deposition. This layer may be covered with photoresist and patterned according to the desired shape of the areas 116 and 130. Unwanted areas of photoresist and seed layer may then be removed by chemical etching. The permeable features may then be deposited over the patterned seed layer by sputtering, plasma deposition or electrochemical plating. It is known that permalloy (80% Ni and 20% Fe), for example, can readily be deposited by electroplating.

Alternatively, a liftoff method may be used to deposit a sheet of permeable material, most of which is then lifted off areas other than 116 and 130. Further details into the lithographic formation of inlaid, magnetically permeable materials may be found in, for example, U.S. Pat. No. 7,229,838. U.S. Pat. No. 7,229,838 is hereby incorporated by reference in its entirety. The substrate may then be planarized by chemical mechanical polishing (CMP), leaving a flat surface for the later bonding of a cover plate.

Having made the permeable features 116 and 130, the movable member or valve 110 and 810 may be formed. The surface may again be covered with photoresist and patterned to protect the inlaid permeable features 116 and 130. The inlet channel 120 and output channels 122 and relieved area 144 may be formed simultaneously with the movable member 110 and 810. With movable member 110, 810 and other areas whose topography is to be preserved covered with photoresist, the features 110, 810, 120, 122 and 144 may be formed by deep reactive ion etching (DRIE) for example.

To form the fluidic channels, a cover plate may be bonded to the surface of the substrate which was previously planarized for this purpose. The cover plate may be optically transparent to allow laser light to be applied to the particles in the fluid stream flowing in the inlet channel 120, and for fluorescence emitted by the fluorescent tags affixed to the particles to be detected by the optical detection system described above. A hole formed in this transparent material may form the waste channel 142. Alternatively, a waste channel 142 may be formed in a second substrate, such as a second silicon substrate, and bonded to the surface of the first substrate. Alternatively, output channel 142 may be formed on the opposite surface of the first substrate using a silicon-on-insulator (SOI) substrate, with waste channel 142 and orifice 140 formed in the handle layer and dielectric layer of the SOI substrate, and the movable feature formed in the device layer.

Additional details for carrying out this process outlined above are well known to those skilled in the art, or readily found in numerous lithographic processing references.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:
1. A micromechanical particle manipulation device, formed on a surface of a substrate, comprising:

a microfabricated, movable member formed on a surface of the substrate in a first plane, and having a first diverting surface, wherein the movable member moves from a first position to a second position in response to a force applied to the movable member, wherein the motion is substantially in the first plane parallel to the surface of the substrate;

a sample inlet channel formed in the substrate and through which a fluid flows, the fluid including target particles and non-target material, wherein the flow in the sample inlet channel is substantially in the first plane parallel to the surface of the substrate;

a sort output channel into which the microfabricated member diverts the target particles and a waste output channel into which the non-target material flows, and wherein the waste output channel is in a second, different plane than the movable member and the sample inlet channel, and wherein the waste output channel is located directly below at least a portion of the microfabricated member over at least a portion of its motion; and a sheath fluid inlet in fluid communication with the sample channel; and a focusing element coupled to the sheath fluid inlet, which is configured to urge the target particles into a particular portion of the sample channel.

2. The micromechanical particle manipulation device of claim 1, wherein focusing element comprises a z-focus channel, wherein the z-focus channel curves in an arc of about 180 degree from the sheath fluid inlet, and urges the target particles into substantially a single plane.

3. The micromechanical particle manipulation device of claim 2, wherein the z-focus channel has a radius of curvature of at least about 100 microns and less than about 500 microns.

4. The micromechanical particle manipulation device of claim 1, wherein the focusing element is disposed in the same plane as the movable member, and formed in the same substrate.

5. The micromechanical particle manipulation device of claim 2, wherein the inlet channel and z-focus channel both have characteristic dimensions of about 50 microns.

6. The micromechanical particle manipulation device of claim 2, further comprising a y-intersection point at which the target particles are compressed from the plane to a stream line near the center of the z-focus channel.

7. The micromechanical particle manipulation device of claim 6, wherein the y-intersection point occurs where two flows join the z-focus channel from substantially antiparallel directions, and each substantially orthogonal to the z-focus channel at the y-intersection point.

8. The micromechanical particle manipulation device of claim 1, wherein the target particles are at least one of a stem cell, a cancer cell, a zygote, a protein, a T-cell, a bacteria, a component of blood, and a DNA fragment.

9. The micromechanical particle manipulation device of claim 1, wherein the first diverting surface has a shape which is substantially tangent to the direction of flow in the input channel at one point on the shape and substantially tangent to the direction of flow of the first output channel at a second point on the shape, and wherein the first diverting surface diverts flow from the input channel into a first output channel when the movable member is in the first position, and allows the flow into the second output channel in the second position.

10. The micromechanical particle manipulation device of claim 1, wherein the plurality of output channels comprises a sort channel and a waste channel, wherein flow in the sort channel is substantially antiparallel to flow in the input channel, and wherein flow in the waste channel is substantially orthogonal to flow in the input channel and the sort channel.

11. The micromechanical particle manipulation device of claim 1, further comprising: a first permeable magnetic material inlaid in the movable member;
a first stationary permeable magnetic feature disposed on the substrate; and
a first source of magnetic flux external to the movable member and substrate on which the movable member is formed.

12. The micromechanical particle manipulation device of claim 11, wherein the movable member moves from the first position to the second position when the source of magnetic flux is activated.

13. The micromechanical particle manipulation device of claim 1, wherein the force is at least one of magnetic, electrostatic, and piezoelectric.

14. A particle manipulation system, comprising:
the micromechanical particle sorting device of claim 1;
at least one laser directed to a laser interrogation region disposed in the input channel; and
at least one set of detection optics that detects a fluorescent signal from a fluorescent tag affixed to the target particle in the fluid.

15. The particle manipulation system of claim 14, further comprising:
an electromagnet; and
a circuit that provides a control waveform to the electromagnet.

16. The particle manipulation system of claim 14, further comprising:
at least one additional laser directed at a region in at least one of the output channels and configured to confirm results of a particle manipulation.

17. The particle manipulation system of claim 15, wherein the control waveform includes a higher amplitude acceleration phase which sets the movable member in motion, a constant amplitude phase which opens the movable member, and a braking phase which slows the movable member at closure.

* * * * *